United States Patent [19]

Holba et al.

[11] Patent Number: 5,276,196

[45] Date of Patent: Jan. 4, 1994

[54] SYNTHESIS OF BIS(HALOARYLSULFONYL) AROMATICS

[75] Inventors: Albert G. Holba, Plano, Tex.; Jim J. Straw, Bartlesville, Okla.; Mel D. Herd, Idaho Falls, Id.

[73] Assignee: Phillips Petroleum Company, Bartlesville, Okla.

[21] Appl. No.: 848,483

[22] Filed: Mar. 9, 1992

[51] Int. Cl.$^5$ .............................. C07C 315/04
[52] U.S. Cl. ...................................... 568/34
[58] Field of Search .......................... 568/34, 35

[56] References Cited

U.S. PATENT DOCUMENTS

| | | | |
|---|---|---|---|
| 2,781,402 | 2/1957 | Chadwick | 260/607 |
| 2,998,454 | 8/1961 | McNichols | 260/607 |
| 3,224,964 | 12/1940 | Huismann et al. | 260/607 |
| 3,402,204 | 9/1968 | Plummer et al. | 568/34 |
| 3,770,832 | 11/1973 | Leslie et al. | 568/34 |
| 4,303,773 | 12/1981 | Gauster | 528/64 |
| 4,990,678 | 2/1991 | Herd et al. | 568/34 |

FOREIGN PATENT DOCUMENTS 0351954 1/1991 European Pat. Off. .

OTHER PUBLICATIONS

Cornell and Tajar ("A New Polyaryl Sulfone Thermoplastic Retaining Mechanical Properties to 400° F.", Society of Plastic Engineers, Tech. Paper 21, 621-3, 1973).

Sulfonylation, "Friedel-Crafts and Related Reactions" Jensen et al, pp. 1319-1347, 1991.

*Primary Examiner*—Marianne M. Cintins
*Assistant Examiner*—Margaret J. Page
*Attorney, Agent, or Firm*—Gary L Haan

[57] ABSTRACT

This invention relates to the synthesis of bis(haloarylsulfonyl) aromatic compounds and more specifically, bis(chlorophenylsulfonyl) aromatic compounds. Bis(chlorophenylsulfonyl) aromatic compounds and particularly 4,4'-bis(4-chlorophenylsulfonyl)biphenyl are frequently used as monomers and comonomers in making high temperature polymers which possess glass transition temperatures greater than 260° C. A process has been developed wherein product of high purity and minimal iron contamination is produced by reacting haloarylsulfonyl halide with an aromatic compound in the presence of an appropriate catalyst with and without solvent.

52 Claims, No Drawings

SYNTHESIS OF BIS(HALOARYLSULFONYL) AROMATICS

BACKGROUND OF THE INVENTION

This invention relates to the synthesis of bis(haloarylsulfonyl) aromatic compounds and more specifically, bis(chlorophenylsulfonyl) aromatic compounds. Bis(chlorophenylsulfonyl) aromatic compounds and particularly 4,4'-bis(4-chlorophenylsulfonyl)biphenyl are frequently used as monomers and comonomers in making high temperature polymers, and specifically polyarylene sulfide polymers which can possess glass transition temperatures greater than 260° C.

Numerous studies have been conducted wherein the Friedel-Crafts sulfonylation reaction is used to synthesize sulfones by the reaction of an arylsulfonyl halide with an aromatic compound in the presence of a Lewis acid catalyst. Of particular interest in this application is the reaction of a halogen-bearing arylsulfonyl chloride with biphenyl. It is widely accepted by those skilled in the art that the presence of an election withdrawing functional group, such as halogen, on either the arylsulfonyl chloride or the aromatic reactant significantly reduces reactivity.

U.S. Pat. No. 4,303,776 teaches that a 45 percent yield of 4,4'-bis(4-chlorophenylsulfonyl)biphenyl is possible when biphenyl is contacted with a stoichiometric excess of 4-chlorobenzene sulfonyl chloride in the presence of a ferric chloride catalyst at a concentration of 0.20 moles catalyst per mole biphenyl reactant and a temperature of 140° C. As the reaction proceeds, the mixture solidifies (see Control Test #1). When using a similar procedure, Cornell and Tajar ("A New Polyaryl Sulfone Thermoplastic Retaining Mechanical Properties up to 400° F.," Society of Plastic Engineers, Tech. Paper 21, 621-3, 1973) report solidification of the mixture and a final yield of 65 percent 4,4'-bis(4-chlorophenylsulfonyl)biphenyl. Cornell et al. note the limitations of a solid final product on process operation and report that nitrobenzene at a concentration of 0.5 to 1.0 parts by weight per weight part biphenyl (0.625 to 1.25 mol/mol) is an excellent solvent for avoiding solidification and improves the yield of 4,4'-bis(4-chlorophenylsulfonyl)biphenyl to greater than 80 percent (see Control Test #2).

European Patent Application 0 351 954 teaches a process for preparing bis(halophenylsulfonyl) benzenoid compounds by reacting p-halosulfonyl halide with a benzonoid compound in an o-dichlorobenzene solvent at 110° to 175° C. and in the presence of ferric chloride catalyst. The resulting precipitate is tan to dark brown in color. The precipitate is then purified by refluxing the reaction mixture with either a hydroxy acid/water, hydroxy acid/alkanol, or a hydroxy acid/water/alkanol mixture at an elevated temperature thereby producing a bis(halophenylsulfonyl) benzenoid compound containing at least 70 ppm iron. The application teaches additional purification via a recrystallization process using an amide or amide/o-dichlorobenzene solvent.

SUMMARY OF THE INVENTION

It is an object of this invention to provide a process for synthesizing bis(haloarylsulfonyl) aromatic compound.

A further object is to provide a process to specifically synthesize 4,4'-bis(4-chlorophenylsulfonyl)biphenyl.

Yet a further object of this invention is to provide a process capable of producing a high purity product which is white in color.

A still further object of this invention is to provide a process capable of producing a product in excellent yield.

And it is yet a further object of this invention to provide a process capable of producing a product containing minimal iron contamination.

In accordance with this invention, a process has been developed wherein product of high purity, minimal iron contamination and white color is produced by reacting haloarylsulfonyl halide with an aromatic species in the presence of a ferric chloride catalyst and nitrobenzene solvent. In another embodiment, an acceptable product is produced by a process wherein haloarylsulfonyl halide is present in stoichiometric excess and apparently functions as both reactant and solvent and ferric chloride is the catalyst. In a third embodiment, acceptable product is obtained by the reaction of haloarylsulfonyl halide and aromatic species in the presence of aluminum chloride catalyst. And in the fourth embodiment, the product yield of embodiment three is improved by using a significant excess of haloarylsulfonyl halide as in embodiment two. All embodiments can additionally comprise a wash step wherein the sulfone reaction product is purified by washing or refluxing with a polar liquid such as acetone and water/acetone and further comprise a recrystallization step wherein the washed sulfone product is recrystallized using methylene chloride at elevated temperatures and pressures.

DETAILED DESCRIPTION OF THE INVENTION

An improved process for the synthesis of high grade sulfone product from the Friedel-Crafts reaction of a haloarylsulfonyl halide with an aromatic compound has been developed. It has been discovered that (1) bis(haloarylsulfonyl) aromatic compound can be prepared by the reaction of haloarylsulfonyl halides, preferably haloarylsulfonyl chlorides, with aromatic compounds at low $FeCl_3$ catalyst concentrations (ex. 0.005 mole $FeCl_3$/mole aromatic), (2) the reaction product with minimal purification meets stringent requirements regarding iron content (i.e., minimal catalyst contamination) and color for polymer-grade monomer, (3) operational properties associated with solidification of the reaction medium are avoided by using either nitrobenzene or excess haloarylsulfonyl halide in the appropriate quantities and (4) the reaction can be catalyzed at elevated temperatures with substoichiometric amounts of $AlCl_3$ catalyst. Desired properties for a polymer-grade monomer possessing acceptable polymerization performance and producing acceptable product are a product purity of 99.5% as determined by high pressure liquid chromatography, an iron content of less than 100 ppm by weight, preferably less than 50 ppm, and most preferably less than 10 ppm, and a white color. Iron present in the monomer detrimentally affects the properties of the polymerized product by adding color and changing the electrical and thermal stability properties of the polymer. The latter are particularly important when making polymers for high temperature applications.

This process is particularly applicable for the synthesis of 4,4'-bis(chlorophenylsulfonyl)biphenyl (BCPSB) which is a monomer or comonomer frequently used in the production of polyaryl sulfone thermoplastics. Such plastics are noted for their thermal stability.

First Embodiment

In the first embodiment, a product of high purity, minimal iron contamination, and white color is obtained by the reaction of haloarylsulfonyl halide, preferably p-haloarylsulfonyl chloride, still more preferably p-chloroarylsulfonyl chloride, with an aromatic species in the presence of a ferric chloride catalyst and nitrobenzene. As an example and most preferably, 4,4′-bis(4-chlorophenylsulfonyl)biphenyl (BCPSB), is prepared by contacting 4-chlorobenzene sulfonyl chloride (CBSC) with biphenyl in the presence of a ferric chloride catalyst and a nitrobenzene solvent. The reaction is represented by

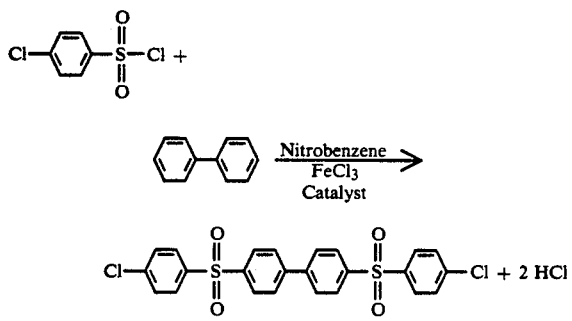

Inventive conditions were determined by a series of experimental tests. The experimental tests were conducted by loading the reactants into a stirred reactor, heating at a constant rate to the desired process temperature, maintaining the process temperature until HCl evolution ceased, cooling the product by quenching and subsequent refluxing with a polar fluid, preferably acetone, filtering the solution to obtain the sulfone product, and washing the filtered solid with a polar fluid, preferably H₂O/acetone and/or acetone to remove impurities which may include reactants, nitrobenzene, colored impurities, catalyst complexed to the unreacted 4-chlorobenzene sulfonyl chloride, 4-(4-chlorophenylsulfonyl)biphenyl, the positional isomers of BCPSB and bis(4-chlorophenyl)sulfone impurities present in the original sulfonyl chloride reactant (see Examples). Because of the detrimental effects of iron on the polymerized monomer product and the difficulties associated with iron removal during monomer purification, a low iron content in the washed sulfone product is particularly desirable.

Inventive conditions were identified by examining the effects of various process parameters on product purity, solids yield, product yield, color and residual iron content. Product purity herein is defined as the weight percentage of bis(haloarylsulfonyl) aromatic compound (ex., BCPSB) in a given sample and was determined using high performance liquid chromatography. Solids yield is defined as the total weight of recovered solids divided by the theoretical weight assuming 100% conversion of the limiting aromatic (ex., biphenyl) reactant to bis(haloarylsulfonyl) aromatic compound. The product yield is defined as the theoretical conversion of the limiting reactant and is calculated by multiplying product purity by solids yield. Iron content was determined using polymer digestion and plasma metals analysis.

Although solids yield is an important process parameter, the purity and the iron content of the final product is even more important because of difficulties associated with purifying the product to polymer grade monomer. On the laboratory scale, Soxhlet extraction with methylene chloride can produce low volume quantities of highly purified product (99.8% purity). However, this purification process is extremely slow and not amenable to scale-up for the treatment of larger quantities. These problems were solved via the development of a high pressure recrystallization process using methylene chloride. The process consists of adding methylene chloride to the product to be purified in a weight ratio of about 4:1, dissolving the product by heating to a temperature of about 140° C. and a pressure of about 210 psig, subsequent recrystallization of purified product by cooling to about 40° to 50° C., filtering the purified solids, washing the solids with a polar fluid, preferably acetone, to remove residual methylene chloride and air drying the purified solid product. Product purities of 99.5% were routinely obtained. However, the purification burden on this process can be significantly reduced by lowering the initial concentration of impurities in the washed polysulfide product feedstream. As previously noted, product impurities from the synthesis of 4,4′-bis(4-chlorophenylsulfonyl)biphenyl typically include the reactants, nitrobenzene, 4-(4-chlorophenylsulfonyl)-biphenyl, organically bound iron, complexed iron, colored impurities, the positional isomers of BCPSB and bis(4-chlorophenyl)sulfone impurities present in the original 4-chlorobenzene sulfonyl chloride reactant. The reaction intermediate, 4-(4-chlorophenylsulfonyl)-biphenyl, is particularly detrimental to polymerization because it can function as a chain terminator.

Presented in Table I for the synthesis of 4,4′-bis(-chlorophenylsulfonyl)biphenyl are solids yield, product purity, product yield and color at 120° and 180° C., a ferric chloride catalyst to biphenyl molar ratio of 0.10 and a nitrobenzene solvent to biphenyl molar ratio of 0.50. For these conditions, the products all possessed some color. Although not wishing to be bound by theory, the grey colors are considered indicative of an excessive heating rate whereby the wall temperatures become too warm and undesirable side reactions occurred. Color can also signify the presence of significant amounts of iron. For this series of tests, the average solids yield, product purity and product yield in percent at 120° F. and 180° F. were 72.0, 90.1, 65.0 and 71.4, 96.1, 67.9, respectively. The overall effect of temperature is small. Temperature (i.e., 120° vs 180° C.) may have had a small effect on product purity but such an effect is not as readily apparent on solids yield and product yield.

Results at similar test conditions but a nitrobenzene solvent to biphenyl molar ratio of 10.0 rather than 0.5 are presented in Table II. For solids yield, product purity and product yield, results at 120° C. were poorer than at 180° C. and for both temperatures, the increase in nitrobenzene solvent to biphenyl molar ratio produced results inferior to those of Table I. No noticable improvement in color characteristics was observed.

Presented in Table III are the inventive results obtained by decreasing the catalyst to biphenyl molar ratio to 0.05, a nitrobenzene solvent to biphenyl molar ratio of 5.25 and a temperature of 150° C. Compared to the results of Table I which were obtained at a greater catalyst to biphenyl molar ratio and lower solvent to biphenyl molar ratio, the solids yield is lower (68.3 versus 72.0 and 71.4%); the product purity is greater (97.9 versus 90.1 and 96.1); the overall product yield is comparable (66.9 versus 65.0 and 67.9%); and the color characteristics of the product are comparable or slightly improved. Although not experimentally confirmed, the iron content at the latter condition is believed to be less because of the factor of two reduction in ferric chloride catalyst concentration. Therefore by operating at the inventive conditions of Table III, an unexpected improvement in product purity (6.8% and 1.8% improvement over Table I values) and reduced iron contamination results. This improvement in product purity significantly reduces the burden on subsequent downstream purification processes for making polymer-grade monomer.

Presented in Table IV are inventive experimental data obtained for a catalyst to biphenyl molar ratio of only 0.005, a solvent to biphenyl molar ratio of 4.0, and a final temperature of 140° C. Three key observations are in order. First, all product produced at these conditions was white in color. Second, product analysis of representative samples indicated an iron concentration of 1.2 and 2.3 ppm by weight (See Example II) which easily meets the most preferred criteria of less than 10 ppm by weight iron for polymer-grade monomer (see Table V). Third, the product purity averaged 96.5% which is only 1.4% less than the value presented in Table III but 6.4 and 0.4% better than average values presented in Table I. The average product yield was 62.0% which is 3.0 to 5.9% less than the Table I and III values and primarily resulted from a lower average solids yield. From an operational perspective, this reduction in product yield is readily compensated for by the significantly lower iron content, the purity of the produced product, and the accompanying reduced load on the downstream purification processes. These results in combination are unexpected.

Presented in Table V is a comparison of results using the prior art synthesizing procedures of Cornell et al. and patent '776 (Control Tests #1 and #2) and the inventive experimental results previously presented in Tables III and IV identified as Inventive Conditions #1 and #2. Although product purity in both Control Tests was excellent (approximately 99.4%), both product samples contained significant color and iron contamination (greater than 200 ppm by weight). The low iron contamination and acceptable product purity and product yields for Inventive Conditions #1 and #2, particularly #2, readily distinguish these processes and the associated operating conditions from the prior art.

Based on the preceeding observations, process conditions not suggested by the prior art have been identified wherein haloarylsulfonyl halides, more preferably haloarylsulfonyl chlorides, can be reacted with aromatic compounds in the presence of a ferric chloride Lewis catalyst thereby producing a bis(haloarylsulfonyl) aromatic compound possessing excellent purity and minimal residual catalyst contamination. The preferred arylsulfonyl chloride is 4-chlorobenzene sulfonyl chloride and the preferred aromatic compound is biphenyl. The haloarylsulfonyl halide must nominally be present in a stoichiometric quantity, a molar ratio of at least 2.0:1 to about 3.0:1 is preferred, 2.0:1 to about 2.5:1 more preferred, and about 2.3:1 most preferred. The ferric chloride catalyst must be present in sufficient quantities to catalyze the reaction but not contaminate the product. A molar ratio of catalyst to aromatic of about 0.0001:1 to about 0.05:1 is preferred, about 0.001:1 to about 0.01:1 more preferred and about 0.005:1 most preferred. To enhance product yield, a nitrobenzene solvent to aromatic molar ratio of 0.05:1 to 10.0:1 is preferred, more preferably 2.0:1 to 8.0:1, still more preferably about 3.75:1 to about 5.5:1, and most preferably about 4.0:1. At this latter ratio, the reactant-bearing solution is approximately 50% by volume nitrobenzene. Although temperature is not a critical parameter, the temperature must be sufficient to insure that appreciable complexation between the iron chloride catalyst and components in the reaction mixture, most notably the sulfone-containing compounds, does not occur. A process temperature of 100° to 200° C. is preferred, 120° to 180° C. more preferred, about 135° to about 155° C. still more preferred, and about 140° C. most preferred. Furthermore, when working at low catalyst to haloarylsulfonyl halide molar ratios (ex., 0.001:1), precautions are required to insure that water does not contaminate the system. Although wishing not to be bound by theory, results suggest that water apparently hydrolyzes haloarylsulfonyl halides to the corresponding sulfonic acids which can effectively complex the ferric chloride catalyst. The solution must also be heated to the final process temperature at a rate sufficiently slow to insure that localized temperatures do not become excessive and thereby result in undesirable side reactions which lead to product discoloration. A reactor skin temperature greater than 220° C. should be avoided. The heating rates are dependent on the size and heat transfer characteristics of the batch reactor and therefore are at the discretion of one skilled in the art. Generally, a heating rate of 0.1° to 7.0° C. per minute is preferred and a rate of about 0.5° to about 1° C. per minute most preferred. The solution should be maintained at the final process temperature until HCl evolution ceases (ex., approximately 3 hours at 140° C.).

In this embodiment and the three embodiments which follow, a bis(haloaryl) aromatic precipitant and a spent liquor are produced by the reaction of haloarylsulfonyl halide with the designated aromatic-bearing hydrocarbons under the designated conditions. The precipitant may then be separated and washed one or more times with a polar liquid to produce a washed precipitant and a spent polar liquid. The washed precipitant may then be further purified by pressure recrystallizing the washed precipitant by contacting with methylene chloride at an elevated temperature and pressure to obtain a purified precipitant product which is of polymer-grade.

Second Embodiment

The second embodiment is similar to the first with the exception that no external solvent (i.e., nitrobenzene) is used in the process and the haloarylsulfonyl halide, preferably haloarylsulfonyl chloride, to aromatic compound molar ratio is increased to at least 2.4:1, preferably about 2.4:1 to about 2.9:1 and most preferably about 2.6:1 to about 2.7:1 (See Example III and Table V, Inventive Condition #3). The most preferred molar ratio is about 2.66:1. Such modifications (1) eliminate the need for handling hazardous solvents (ex., nitrobenzene) (2) provide sufficient excess haloarylsulfonyl halide reactant such that a reaction medium capable of being stirred and pumped is maintained thereby avoiding the solidification problems reported in the prior art for a CBSC to biphenyl molar ratio of 2.3:1, and (3) unexpectedly results in conversions of 80% at a catalyst to biphenyl molar ratio of about 0.005:1. The results are unexpected in view of prior art conversions of only 45 to 65% at a greater catalyst to biphenyl molar ratio of 0.20 and a haloarylsulfonyl halide to biphenyl molar ratio of 2.3:1. Increasing the haloarylsulfonyl halide to biphenyl molar ratio from 2.3:1 to 2.7:1 increases the reaction medium volume by less than 12%.

Compared to the first embodiment wherein the addition of nitrobenzene at preferred conditions doubled the volume of the reaction medium, addition of excess halogenated arylsulfonyl halide which increased the reaction medium volume by less than 12% surprisingly resulted in an increase in yield by greater than 10%. Acceptable solids yield, product purity and product yield indicate a process temperature of 100° to 200° C. and a catalyst to aromatic-bearing hydrocarbon molar ratio of about 0.001:1 to about 0.01:1 are preferred. White product indicative of less than 50 ppm by weight iron content and acceptable solids yield, product purity and product yield are obtained at more preferred conditions (see Table VI) which include a catalyst to biphenyl molar ratio of about 0.001:1 to about 0.0053:1 and temperatures of 120° to 190° C. A most preferred temperature for process operation is about 140° to about 160° C. and a most preferred temperature is about 150° C. As in the preceding embodiment, polar fluids are used to quench the reaction and wash the sulfone product. However in the current embodiment wherein no solvent is used (i.e., a neat reaction), polar fluid added during quenching also functions as an excellent diluent, thereby preventing the product mixture from becoming highly viscous on cooling and thus aiding the solids separation step.

Third Embodiment

In the third embodiment, acceptable product is obtained by the reaction of haloarylsulfonyl halide, preferably haloarylsulfonyl chloride, and aromatic species in the presence of AlCl$_3$ catalyst (See Example IV). This embodiment is distinguishable from the prior art teachings of '776 and Cornell et al. in that low color (i.e., white), low iron content and acceptable yields are achieved by using very small amounts of AlCl$_3$ as a Lewis acid catalyst at an elevated temperatures (ex., 180° F.). Wishing not to be bound by theory, the elevated temperatures apparently reduce the degree of catalyst/sulfone complexation thereby enabling operation at nonstoichiometric catalyst to haloarylsulfonyl halide molar ratios. A similar phenomenom apparently occurs when FeCl$_3$ is used as a catalyst but because of a weaker complex, lower operating temperatures (ex., 140° F.) are possible. Control Test #3 teaches that extension of the preceding observations to a system further comprising nitrobenzene is unsuccessful. Although wishing not be bound by theory, the poor yield apparently results from AlCl$_3$ catalyst:nitrobenzene complexation at these conditions.

Experimental results for the synthesis of 4,4'-bis(4-chlorophenylsulfonyl)biphenyl by the Friedel-Crafts sulfonylation of biphenyl with 4-chlorobenzenesulfonyl chloride in the presence of low AlCl$_3$ catalyst concentrations are presented in Table VII. The results teach that an acceptable product and yields of 57 to 64% are possible when using aluminum chloride at nonstoichiometric catalyst to biphenyl ratios, elevated temperatures and a stoichiometric excess of 4-chlorobenzene sulfonyl chloride. Furthermore, product yields of 57 to 64% are comparable to the "prior art" data for FeCl$_3$ catalyst wherein yields of 45 to 65% were reported for products that contained excessive color and iron contamination. The results for this embodiment are only slightly poorer than results obtained for the inventive sulfonylation reaction disclosed herein as the first embodiment wherein nitrobenzene is used as a solvent and the FeCl$_3$ catalyst concentration is reduced 40-fold from the prior art. As in the second embodiment, a polar fluid, preferably acetone, functions as an excellent diluent, quench and reflux fluid. Furthermore polar fluids, preferably acetone and water/acetone mixtures, function as excellent wash fluids for the filtered sulfone product.

For the AlCl$_3$ catalyzed reaction, an excess stoichiometric ratio of haloarylsulfonyl chloride to aromatic compound is preferred. A molar ratio of greater than 2.0:1 to about 2.4:1 is more preferred and a ratio of about 2.3:1 is most preferred. The preferred temperature range is 100° to 200° C., more preferred is about 150° to about 200° C. and the most preferred temperature is about 180° C. Because AlCl$_3$ has a less detrimental effect on monomer properties and subsequent polymerization, catalyst concentrations are not as critical. The minimal amount of catalyst effective to catalyze the reaction at said process temperature is preferred. A molar ratio of catalyst to aromatic of about 0.01:1 to about 0.10:1 is more preferred and about 0.06:1 most preferred.

Fourth Embodiment

The fourth embodiment combines the experimental results of the second embodiment wherein yield is substantially improved by using a significant excess of haloarylsulfonyl halide, preferably haloarylsulfonyl chloride, such that the haloarylsulfonyl halide can apparently function as a solvent thereby facilitating the reaction and the experimental observations of the third embodiment wherein the sulfonylation reaction is catalyzed by nonstoichiometric amounts of AlCl$_3$ at elevated temperatures. Based on these observations which are not available in the prior art, one skilled in the art readily recognizes that the yield in the third embodiment (i.e., the AlCl$_3$ catalyzed process) can be significantly enhanced by operating at the solvent conditions of the second embodiment. Therefore, the preferred haloarylsulfonyl chloride to aromatic-bearing hydrocarbon ratio is about 2.4:1 to about 2.8:1 and the most preferred ratio is about 2.7:1. As in the second embodiment, a polar fluid, preferably acetone, functions as an excellent diluent, quench and reflux fluid. Furthermore polar fluids, preferably acetone and water/acetone mixtures, function as excellent wash solutions for the filtered sulfone product.

Although the preceding embodiments focus primarily on the batch preparation of bis(haloarylsulfonyl) aromatics, the extension of said concepts to semi-continuous or continuous processes is readily within the realm of one skilled in the art. Such processes which might include, but shall not be limited to, the use of continuous reactors such as stirred tank reactors in series, tubular reactors, and fluidized bed reactors; the use of solids separation devices such as cyclones, rotary drums, and filters with back-wash capabilities; and the use of continuous solid dryers such as heated fluidized beds, drum dryers, and belt dryers.

The following examples are provided to illustrate the practice of the invention and are not intended to limit the scope of the invention or the appended claims in any way.

Control Test #1

The following test was conducted as a control run using a procedure similar to that disclosed in U.S. Pat. No. 4,303,776 wherein:

| Molar Ratio FeCl$_3$:Biphenyl | Molar Ratio CBSC:Biphenyl |
|---|---|
| 0.1850:1 | 2.28:1 |

A 1.5-liter 4-necked round-bottomed flask fitted with a reflux condenser, mechanical stirring device, Hastalloy C thermocouple well and nitrogen inlet means was charged with the following components: 77 grams (0.5 mole) biphenyl and 239.9 grams (1.14 moles) of 4-chlorobenzenesulfonyl chloride.

The stirred reaction mass containing no external (non-reacting) solvent was heated to a temperature of about 70° C. over a period of 30 minutes at which time 15 grams (0.0925 mole) of anhydrous ferric chloride was added. The reaction temperature was increased to about 140° C. in a period of one hour at which time the mixture was too thick to stir. Heating was continued for approximately two hours to give a total reaction time of about 3 hours.

After removing the heat source, the reaction was quenched by the addition of 300 mL of N,N-dimethylformamide (DMF). The stirred mixture was cooled to 20° C. and the precipitated product was separated by filtration. The experimental procedure at this point departed slightly from that disclosed in '776. Rather than dissolving and recrystallizing with DMF, the solid was washed successively with acetone, 10 vol % water in acetone and then finally with acetone. The light yellow colored 4,4'-bis(4-chlorobenzenesulfonyl)biphenyl weighed 136 grams (54.0% solids yield) and possessed a purity of 99.4% (53.6% product yield) as determined by high pressure liquid chromatography. The residual iron in this product was 210 ppm by weight.

The yield of 53.6 is greater than the 45% yield reported in U.S. Pat. No. 4,303,776 and less than the 65% yield reported by Cornell and Tajar. The iron contamination in the product of 210 ppm by weight is much greater than that considered acceptable for polymer-grade monomer.

Control Test #2

The following test was conducted as a control run using a procedure similar to that taught by Cornell and Tajar wherein:

| Molar Ratio FeCl$_3$:Biphenyl | Molar Ratio CBSC:Biphenyl | Molar Ratio $\phi$NO$_2$:Biphenyl |
|---|---|---|
| 0.194:1 | 2.25:1 | 6.12:1 |

A 5-liter 4-necked round-bottomed flask fitted with a reflux condenser, Hastalloy C thermocouple well, mechanical stirring device and nitrogen inlet means was charged with the following components: 154.2 grams (1 mole) of biphenyl, 474.9 grams (2.25 moles) of 4-chlorobenzenesulfonyl chloride (CBSC) and 630 mL (6.12 moles) of nitrobenzene solvent.

The stirred reaction mixture was heated to a temperature of about 70° C. over a period of 30 minutes at which time 31.5 grams (0.194 mole) of anhydrous ferric chloride was added. The reaction temperature was increased to about 130° C. in a period of one hour and then maintained at about that temperature for another four hours. At this point, the procedure differed from that disclosed by Cornell and Tajar. Rather than quenching with DMF, cooling, filtering and subsequent purification via recrystallization with DMF, an acetone quench with 200 mL was conducted after the five hour reaction period. The precipitated product was removed by filtration and washed successively with acetone, 10 vol % water in acetone and finally another portion of acetone. The dried dark gray colored 4,4'-bis(4-chlorobenzenesulfonyl)biphenyl weighed 373.2 grams (74.0% solids yield) and possessed a purity of 99.4% (73.6% product yield) as determined by high pressure liquid chromatography. The product was a very dark grey and residual iron in this product was 803 ppm by weight.

The yield of 73.6% is slightly less than the 80% reported by Cornell and Tajar. The iron contamination of 803 ppm by weight is considered excessive for polymer-grade monomer which most preferably has an iron content of less than 10 ppm by weight.

Control Test #3

Attention is called to the following parameters related to this noninventive run:

| Molar Ratio AlCl$_3$:Biphenyl | Molar Ratio CBSC:Biphenyl | Molar Ratio Solvent:Biphenyl |
|---|---|---|
| 0.060:1 | 2.3:1 | 4.88:1 |

A 1.5-liter 3-necked glass resin flask fitted with a reflux condenser, mechanical stirring device and nitrogen inlet means was charged with the following components: 77.1 grams (0.5 mole) of biphenyl, 242.7 grams (1.15 moles) of 4-chlorobenzenesulfonyl chloride, 4 grams (0.03 mole) of aluminum chloride and 300.5 grams (2.44 moles) of nitrobenzene solvent.

The stirred reaction mixture was heated to a temperature of about 140° C. over a period of 2 hours. The system was maintained at this temperature for one hour and then the temperature was increased to about 160° C. After holding the temperature at 160° C. for about one hour, the temperature was raised to 180° C. The reaction temperature was maintained at 180° C. for about an hour to give a total reaction period of about 6.66 hours.

The reaction mixture was cooled to about 120° C. and quenched by the addition of 300 mL of acetone. After stirring this mixture for 10 minutes, the temperature had decreased to 60° C. and the solid product was removed by filtration. The solid was washed successively with 200 mL, 400 mL and 400 mL portions of acetone. The light gray colored product after drying weighed 100.5 grams (39.9% solids yield) and exhibited a purity of 87.89% (35.1% product yield) as determined by high pressure liquid chromatography.

The poor yield and poor product purity in this test demonstrates that the apparently obvious extrapolation of prior art results and the inventive results presented in Examples I through IV, particularly Example IV, to the above process conditions is not valid.

EXAMPLE I

Attention is called to the following parameters related to this inventive run concerning the preparation of 4,4'-bis(4-chlorobenzenesulfonyl)biphenyl in the presence of ferric chloride catalyst and nitrobenzene solvent:

| Molar Ratio FeCl$_3$:Biphenyl | Molar Ratio CBSC:Biphenyl | Molar Ratio $\phi$NO$_2$:Biphenyl |
|---|---|---|
| 0.05:1 | 2.5:1 | 5.25:1 |

A 1.5-liter 4-necked glass resin flask fitted with a reflux condenser, Hastalloy C thermocouple well, mechanical stirring device and nitrogen inlet means was charged with the following components: 77.1 grams (0.5 mole) of biphenyl, 263.8 grams (1.25 moles) of 4-chlorobenzenesulfonyl chloride, 4.15 grams (0.0256 mole) of iron chloride and 269.3 mL (2.63 mole) of nitrobenzene.

The stirred reaction mixture was heated to a temperature of about 150° C. at a 1° C./min ramp rate and maintained at the final temperature for 2.5 hrs.

The reaction mixture was cooled to about 90° C. and quenched by the controlled addition of 200 mL of acetone over a 10 minute period. Because the boiling point of acetone is 56.2° C. at 1 atmosphere, significant refluxing of fluids in the water-cooled reflux condenser was observed upon acetone addition. The reflux condenser also served to remove heat from the system. The mixture was stirred for 10 minutes to further cool the reaction mass to about 60° C. before removing the product by filtration. The product was then washed with 200 mL of 10 vol % water in acetone, followed by another 200 mL acetone wash and air dried to a light tan solid which weighed 167.0 grams for a solids yield of 66.5% and possessed a purity of 97.5% for a product yield of 64.6% as determined by high pressure liquid chromatography.

The resulting product yield and product purity is comparable to prior art values conducted at much greater iron chloride catalyst concentrations.

TABLE I[a]

Catalyst:Biphenyl Mole Ratio: 0.10:1
Nitrobenzene:Biphenyl Mole Ratio: 0.50:1
CBSC:Biphenyl Mole Ratio: 2.30:1

|  | Temperature | Solids Yield | Product Purity | Product Yield | Color |
|---|---|---|---|---|---|
|  | 120° C. | 72.1% | 90.1% | 65.0% | light tan |
|  | 120 | 66.8 | 88.8 | 59.3 | tan |
|  | 120 | 77.2 | 91.5 | 70.6 | — |
| Average | 120 | 72.0 | 90.1 | 65.0 |  |
| Standard Deviation | 0.0 | 5.20 | 1.35 | 5.65 |  |
|  | 180° C. | 74.3% | 92.6% | 68.8% | light yellow |
|  | 180 | 72.7 | 97.5 | 70.9 | grey |
|  | 180 | 67.2 | 98.3 | 66.1 | tan |
| Average | 180 | 71.4 | 96.1 | 67.9 |  |
| Standard Deviation | 0.0 | 3.72 | 3.78 | 2.55 |  |

[a]Noticeable color was observed in all runs where reported. Temperature had a nominal effect on product properties.

EXAMPLE II

Attention is called to the following parameters related to this inventive run concerning the preparation of 4,4'-bis(4-chlorobenzenesulfonyl)biphenyl in nitrobenzene solvent in the presence of ferric chloride catalyst:

| Molar Ratio FeCl₃:Biphenyl | Molar Ratio CBSC:Biphenyl | Molar Ratio ØNO₂:Biphenyl |
|---|---|---|
| 0.0052:1 | 2.30:1 | 4.05:1 |

A 22-liter 4-necked round-bottomed flask fitted with a reflux condenser, mechanical stirring device, Hastalloy C thermocouple well and nitrogen inlet means was charged with the following components: 1856 grams (12.03 moles) of biphenyl, 5854 grams (27.73 moles) of 4-chlorobenzenesulfonyl chloride (CBSC), 10.2 grams (0.063 moles) of anhydrous ferric chloride and 5 liters (48.7 moles) of nitrobenzene solvent. An initial endotherm to −3° C. was observed as stirring began.

The stirred reaction mixture was gradually heated to a maximum temperature of 140° C. as the evolution of HCl signaled that the reaction was taking place. The reaction temperature was 81° C. at the end of one hour, 101° C. at the end of two hours, 120° C. at the end of three and four hours, and 140° C. at the end of 5 hours where it remained until HCl evolution essentially ceased some 2.5 hours later. As the reaction took place, the dark yellowish-red reaction mass turned dark green and a white crystalline product precipitated.

At the end of the 7.5 hour reaction period, the reaction mixture was cooled to about 100° C. Four liters of acetone was then added under controlled conditions and fluid refluxing observed. When the quenched reaction mixture cooled to about 60° C., the white colored product was removed by filtration and washed successively with 4 liters of acetone, 4 liters of 10 vol % water in acetone and finally with another 4 liter portion of acetone. The crude product was air dried to remove acetone.

The dried product comprising 4,4'-bis(4-chlorobenzenesulfonyl) biphenyl weighed 4022.1 grams (66.5% solids yield) and possessed a product purity of 95.47% (63.5% product yield). Iron content was 1.18 ppm by weight as determined using polymer digestion and plasma metals analysis. This yield compares favorably with prior art values and the iron content of the product easily meets the most preferred criteria of less than 10 ppm by weight for polymer-grade monomer.

Another test conducted under similar conditions gave a solids yield of 62.7%, a product purity of 96.4%, a product yield of 60.5%, and an iron content of 2.34 ppm.

TABLE II[a]

Catalyst:Biphenyl Mole Ratio: 0.10:1
Nitrobenzene:Biphenyl Mole Ratio: 10.0:1
CBSC:Biphenyl Mole Ratio: 2.30:1

|  | Temperature | Solids Yield | Product Purity | Product Yield | Color |
|---|---|---|---|---|---|
|  | 120° C. | 46.6% | 56.4% | 26.3% | tan |
|  | 120 | 58.0 | 56.1 | 32.6 | — |
| Average | 120 | 52.3 | 56.25 | 29.45 |  |
| Standard Deviation | 0.0 | 8.06 | 0.21 | 4.45 |  |
|  | 180° C. | 64.5% | 77.9% | 50.3% | tan |
|  | 180 | 60.0 | 98.1 | 58.8 | grey |
|  | 180 | 62.5 | 58.0 | 36.2 | — |
|  | 180 | 62.5 | 97.9 | 61.2 | light yellow |
|  | 180 | 71.7 | 62.5 | 44.8 | grey |
| Average | 180 | 64.2 | 78.8 | 50.3 |  |
| Standard Deviation | 0.0 | 4.47 | 18.9 | 10.2 |  |

[a]Where reported, all product possessed undesirable color. Results were generally poorer at 120° C. than at 180° C. The increase in nitrobenzene ratio from that reported in Table 1 resulted in generally poorer performance.

EXAMPLE III

Attention is called to the following parameters related to this inventive run concerning the preparation of 4,4'-bis(4-chlorbenzenesulfonyl)biphenyl in the presence of ferric chloride catalyst and without an external solvent:

| Molar Ratio FeCl₃:Biphenyl | Molar Ratio CBSC:Biphenyl | Molar Ratio Solvent:Biphenyl |
|---|---|---|
| 0.0015:1 | 2.68:1 | 0.0:1 |

A 5-liter 3-necked glass resin flask fitted with a reflux condenser, mechanical stirring device and nitrogen inlet means was charged with the following components: 555.2 grams (3.5 moles) of biphenyl, 2032.6 grams (9.36 moles) of 4-chlorobenzenesulfonyl chloride (CBSC) and 0.864 gram (0.0053 mole) of anhydrous ferric chloride.

The stirred reaction mixture was gradually heated to a temperature of about 150° C. over a period of about 3 hours. The system was maintained at this temperature for an additional hour before increasing the temperature of the reaction mass to about 160° C. The temperature was maintained at 160° C. for an additional 2.25 hours to give a total reaction time of about 6.25 hours. The evolution of HCl had essentially stopped at the end of the reaction period.

The stirred reaction mixture was allowed to cool to 135° C. before the controlled addition of one liter acetone. Upon the controlled addition of acetone, significant refluxing of fluids in the water-cooled reflux condenser was observed. The system was stirred for 15 minutes as the temperature decreased to 45° C. The product was removed by filtration and washed successively with acetone, a 10:90 vol:vol water:acetone mixture and finally 4 liters of acetone. The dried white solid product weighed 1413 grams (80.1%) solids yield) and possessed a purity of 96% (76.9% product yield) as determined by high pressure liquid chromatography.

A yield comparable to and in certain situations superior to prior art values was obtained without hazardous (nitrobenzene) solvent. The low ferric chloride catalyst concentration and the white product color indicate the product met the preferred criteria of less than 50 ppm by weight iron for polymer-grade monomer.

TABLE III[a]

Catalyst:Biphenyl Mole Ratio: 0.05:1
Nitrobenzene:Biphenyl Mole Ratio: 5.25:1
CBSC:Biphenyl Mole Ratio: 2.30:1

| Temperature | Solids Yield | Product Purity | Product Yield | Color |
|---|---|---|---|---|
| 150° C. | 66.5% | 97.5% | 64.8% | light tan |
| 150 | 68.3 | 98.3 | 67.2 | grey |
| 150 | 65.7 | 97.0 | 63.7 | tan |
| 150 | 69.7 | 98.5 | 68.7 | grey |
| 150 | 67.7 | 98.6 | 66.7 | — |
| 150 | 69.7 | 97.2 | 67.8 | tan |
| 150 | 68.3 | 98.5 | 67.3 | light grey |
| 150 | 67.5 | 96.9 | 65.4 | grey |
| 150 | 72.0 | 99.1 | 71.5 | — |
| 150 | 67.2 | 97.0 | 65.2 | tan |
| 150 | 69.0 | 98.5 | 67.9 | light tan |
| Average 150 | 68.3 | 97.9 | 66.9 | |
| Standard Deviation 0.0 | 1.8 | 0.81 | 2.1 | |

[a]Although the solids yield is generally less than that reported in Table I, product purity and product yield is generally greater. Although not experimentally confirmed, the iron content of product for the Table III conditions is believed to be significantly less than for the Table I conditions because of the corresponding factor of 2 reduction in iron chloride catalyst concentration.

EXAMPLE IV

Attention is called to the following paramaters related to this inventive run concerning the preparation of 4,4'-bis(4-chlorobenzenesulfonyl)biphenyl in the presence of aluminum chloride catalyst and without an external solvent:

| Molar Ratio AlCl₃:Biphenyl | Molar Ratio CBSC:Biphenyl | Molar Ratio Solvent:Biphenyl |
|---|---|---|
| 0.060:1 | 2.3:1 | 0.0:1 |

A 1.5-liter 3-necked glass resin flask fitted with a reflux condenser, mechanical stirring device and nitrogen inlet means was charged with the following components: 77.1 grams (0.5 mole) of biphenyl, 242.7 grams (1.15 moles) of 4-chlorobenzenesulfonyl chloride and 4 grams (0.03 mole) of aluminum chloride.

The stirred reaction mixture was heated to a temperature of about 180° C. over a period of about 2.5 hours. The system was maintained at this temperature for an additional two hours to give a total reaction time of about 4.5 hours.

The reaction mixture was cooled to about 140° C. and slowly quenched by the controlled addition of 400 mL of acetone over a 10 minute period. Upon the controlled addition of acetone, significant refluxing of fluids in the water-cooled reflux condenser was observed. The mixture was stirred for 10 minutes to further cool the reaction mass to about 50° C. before removing the product by filtration. The product was washed with 600 mL of acetone and air dried to a white solid which weighed 165.7 grams (65.8% solids yield) and possessed a purity of 97.6% (64.2% product yield) as determined by high pressure liquid chromatography.

A duplicate run with a reaction period of 5.5 hours gave an air-dried white product which weighed 159 grams (63.3% yield).

The results indicate that acceptable yields and product containing no iron contamination are possible via this process wherein no hazardous solvent is used.

TABLE IV[a]

Catalyst:Biphenyl Mole Ratio: 0.005:1
Nitrobenzene:Biphenyl Mole Ratio: 4.05:1
CBSB:Biphenyl Mole Ratio: 2.30:1

| Temperature | Solids Yield | Product Purity | Product Yield | Color |
|---|---|---|---|---|
| 140° C. | 64.6% | 97.0% | 62.7% | white |
| 140 | 64.4 | 96.8 | 62.4 | white |
| 140 | 62.7 | 96.4 | 60.5 | white |
| 140 | 66.7 | 96.7 | 64.5 | white |
| 140 | 63.1 | 96.1 | 60.6 | white |
| 140 | 61.1 | 95.8 | 58.5 | white |
| 140 | 67.0 | 96.6 | 64.7 | white |
| Average | 64.2 | 96.5 | 62.0 | |
| Standard Deviation | 2.1 | 0.43 | 2.3 | |

[a]The white color of product is indicative of a polymer-grade monomer. A representative sample analysis indicated 1.2 and 2.3 ppm by weight iron (See Example II). Product purity is comparable to the values reported in Table III. Product yield is less because of lower solids yield.

TABLE V

| | Nitrobenzene/Biphenyl Mole Ratio | FeCl₃/Biphenyl Mole Ratio | Solids Yield | Product Purity | Product Yield | Iron ppm (wt) | Color |
|---|---|---|---|---|---|---|---|
| | | Product Characteristics | | | | | |
| Control Test #1[a] | 6.12:1 | 0.194:1 | 73.6 | 99.4% | 73.2 | 803 | dark grey |
| Control Test #2[b] | 0.0:1 | 0.185:1 | 53.8 | 99.4 | 53.5 | 210 | light yellow |
| Inventive Condition #1[c] | 5.25:1 | 0.05:1 | 68.3 | 97.9 | 66.9 | — | grey, tan, light grey, light tan |
| Inventive Condition #2[d] | 4.05:1 | 0.0052:1 | 64.2 | 96.5 | 62.0 | 1.2 | white |
| Inventive Condition #3[e] | 0.0:1 | 0.0015:1 | 78.0 | 96.0 | 74.5 | — | white |

[a]Control test conducted at prior art condition disclosed by Cornell et al.
[b]Control test conducted at prior art condition disclosed in U.S. Pat. No. 4,303,776.
[c]See Example I also Table III, CBSC:Biphenyl mole ratio: 2.30.
[d]See Example II and also Table IV, CBSC:Biphenyl mole ratio: 2.30.
[e]See Example III and also Table VI, CBSC:Biphenyl mole ratio: 2.68.

TABLE VI
Solventless Process[a]

| Temp. (°C.) | Catalyst[b] Ratio | CBSC[c] Ratio | Solids Yield | Product Purity | Product Yield | Color |
|---|---|---|---|---|---|---|
| 140[d] | .0053:1 | 2.68:1 | 76.6% | 96.4% | 73.8% | white |
| 150[e] | .0053:1 | 2.68:1 | 76.7 | 94.9 | 72.8 | white |
| 150[f] | .0053:1 | 2.80:1 | 81.4 | 97.3 | 79.2 | white |
| 150[f] | .0053:1 | 2.80:1 | 80.0 | 98.1 | 78.5 | white |
| 160[e] | .0035:1 | 2.68:1 | 78.6 | 94.6 | 74.4 | white |
| 160[e] | .0026:1 | 2.68:1 | 75.7 | 96.2 | 72.8 | white |
| 160[e] | .0020:1 | 2.68:1 | 73.2 | 95.4 | 69.8 | white |
| 160[e] | .0015:1 | 2.68:1 | 78.0 | 96.0 | 74.5 | white |
| 160[e] | .0011:1 | 2.68:1 | 73.0 | 96.3 | 70.3 | white |
| 170 | .0078:1 | 2.86:1 | 64.7 | 96.6 | 62.5 | off-white |
| 170[g] | .0052:1 | 2.66:1 | 61.0 | 95.7 | 58.4 | off-white |
| 170[h] | .0010:1 | 2.25:1 | 59.0 | 96.2 | 56.8 | white |
| 170[h] | .0008:1 | 2.25:1 | 55.6 | 96.2 | 53.5 | white |
| 180[h] | .0078:1 | 2.30:1 | 71.0 | 98.3 | 69.8 | light yellow |
| 180 | .0078:1 | 2.86:1 | 71.4 | 97.6 | 69.7 | off-white |
| 180 | .0078:1 | 2.86:1 | 65.9 | 97.9 | 64.5 | off-white |
| 180 | .0078:1 | 2.86:1 | 64.7 | 96.6 | 62.5 | off-white |
| 180 | .0078:1 | 2.66:1 | 71.7% | 98.3% | 70.5% | off-white |
| 180 | .0052:1 | 2.66:1 | 71.3 | 97.7 | 69.7 | white |
| 180 | .0052:1 | 2.66:1 | 73.5 | 97.6 | 71.7 | white |
| 190 | .0052:1 | 2.66:1 | 75.0 | 99.2 | 74.4 | white |
| 190 | .0052:1 | 2.66:1 | 73.3 | 98.1 | 71.9 | white |
| 200 | .0052:1 | 2.33:1 | 69.0 | 98.8 | 68.1 | off-white |

[a]Unless noted, all tests conducted in 1.5 L glass reactors.
[b]Catalyst to biphenyl mole ratio.
[c]CBSC to biphenyl mole ratio.
[d]12 L glass reactor.
[e]5 L glass reactor.
[f]2 gal Hastalloy C stirred tank reactor, agitation speed - 200 to 650 rpm.
[g]3 L glass reactor
[h]Very thick slurry/solid mass was formed.
The white product color and associated results conclusively establish conditions wherein polymer-grade monomer can be produced in the absence of hazardous nitrobenzene solvent.

TABLE VII
Sulfonylation Reaction Using AlCl₃ Catalyst

| Temp. (°C.) | Catalyst Ratio | CBSC Ratio | Solids Yield | Product Purity | Product Yield | Color |
|---|---|---|---|---|---|---|
| 180[a] | .06:1 | 2.30:1 | 65.8% | 97.6% | 64.2% | white |
| 190 | .06:1 | 2.30:1 | 63.3 | 96.2 | 60.9 | white |
| 180 | .09:1 | 2.30:1 | 59.5 | 96.7 | 57.6 | white |
| 180[b] | .06:1 | 2.30:1 | 40.0 | 87.9 | 35.2 | light gray |

[a]See Example IV.
[b]See Example V, Nitrobenzene:Biphenyl mole ratio of 4.9:1.
Results establish conditions wherin polymer-grade monomer can be produced using aluminum chloride as a catalyst in the absence of hazardous (nitrobenzene) solvent.

That which is claimed is:

1. A process for making white bis(haloarylsulfonyl) aromatic compounds comprising the steps of (a) contacting a stoichiometric excess of haloarylsulfonyl halide with an aromatic-bearing hydrocarbon selected from the group consisting of unsubstituted aromatics and alkyl-substituted aromatic compounds in the presence of nitrobenzene solvent at a solvent to aromatic-bearing hydrocarbon molar ratio of 0.05:1 to 10:1, a process temperature in the range of 100° to 200° C., and in the presence of a ferric chloride catalyst wherein ferric chloride catalyst to aromatic-bearing hydrocarbon molar ratio is about 0.001:1 to about 0.01:1, thereby producing a precipitant and a spent liquor as products, (b) cooling said products by quenching and refluxing with a first polar fluid, (c) separating said precipitant, and (d) washing said precipitant one or more times with a second polar fluid to obtain a white precipitant and a spent polar liquid.

2. A process according to claim 1 wherein the haloarylsulfonyl halide to aromatic-bearing hydrocarbon molar ratio is at least 2.0:1 to about 3.0:1 and said haloarylsulfony halide is a haloarylsulfonyl chloride and said second polar fluid is acetone or an acetone/water mixture.

3. A process according to claim 2 wherein said nitrobenzene solvent to aromatic-bearing hydrocarbon molar ratio is about 3.75:1 to about 5.0:1.

4. A process according to claim 3 wherein said process temperature is in the range of about 135° to about 155° C.

5. A process according to claim 4 wherein said aromatic-bearing hydrocarbon is an unsubstituted aromatic compound and said haloarylsulfonyl chloride is a 4-halobenzene sulfonyl chloride.

6. A process according to claim 5 wherein said ferric chloride catalyst to aromatic-bearing hydrocarbon molar ratio is about 0.005:1.

7. A process according to claim 6 wherein said aromatic-bearing hydrocarbon is biphenyl.

8. A process according to claim 7 wherein said haloarylsulfonyl chloride is 4-chlorobenzene sulfonyl chloride.

9. A process for making white 4,4'-bis(4-chlorophenylsulfonyl)biphenyl comprising the steps of (a) contacting 4-chlorobenzene sulfonyl chloride with biphenyl at a stoichiometric molar ratio of about 2.3:1, said contacting being in the presence of nitrobenzene at a nitrobenzene to biphenyl molar ratio of about 4.0:1, in the presence of ferric chloride catalyst at a catalyst to biphenyl molar ratio of about 0.005:1, and at a process temperature of about 140° C. thereby producing a precipitant and a spent liquor as products, (b) cooling said products by quenching and refluxing with a first polar fluid, (c) separating said precipitant, and (d) washing said precipitant one or more times with a second polar fluid to obtain a white precipitant and a spent polar liquid.

10. A process according to claim 9 wherein said second polar fluid is acetone or an acetone/water mixture.

11. A process for making white bis(haloarylsulfonyl) aromatic compounds comprising the steps of (a) contacting haloarylsulfonyl halide in the absence of an extraneous solvent with aromatic-bearing hydrocarbon selected from the group consisting of unsubstituted aromatic compounds and alkyl-substituted aromatic compounds wherein the haloarylsulfonyl halide to aromatic-bearing hydrocarbon molar ratio is at least 2.4:1, the process temperature is in the range of 100° to 200° C., and in the presence of a ferric chloride catalyst wherein the ferric chloride catalyst to aromatic-bearing hydrocarbon molar ratio is about 0.001:1 to about 0.01:1, thereby producing a precipitant and a spent liquor as products, (b) cooling said products by quenching and refluxing with a first polar fluid, (c) separating said precipitant, and (d) washing said precipitant one or more times with a second polar fluid to obtain a white precipitant and a spent polar liquid.

12. A process according to claim 11 wherein said haloarylsulfonyl halide to aromatic-bearing hydrocarbon ratio is about 2.4:1 to about 2.9:1, said process temperature is in the range of about 120° to about 190° C., said haloarylsulfonyl halide is a haloarylsulfonyl chloride, and said second polar fluid is acetone or an acetone/water mixture.

13. A process according to claim 12 wherein said haloarylsulfonyl halide to aromatic-bearing hydrocarbon molar ratio is about 2.6:1 to about 2.7:1.

14. A process according to claim 13 wherein said aromatic-bearing hydrocarbon is an unsubstituted aromatic compound and said haloarylsulfonyl chloride is a 4-halobenzene sulfonyl chloride.

15. A process according to claim 14 wherein said aromatic-bearing hydrocarbon is biphenyl.

16. A process according to claim 15 wherein said haloarylsulfonyl chloride is 4-chlorobenzene sulfonyl chloride.

17. A process for making white 4,4'-bis(4-chlorophenylsulfonyl)biphenyl comprising the steps of (a) contacting 4-chlorobenzene sulfonyl chloride with biphenyl at a stoichiometric molar ratio of about 2.66:1 in the presence of a ferric chloride catalyst at a catalyst to biphenyl molar ratio of about 0.005:1, and a process temperature of about 150° C. thereby producing a precipitant product and a spent liquor as products, (b) cooling said products by quenching and refluxing with a first polar fluid, (c) separating said precipitant, and (d) washing said precipitant product one or more times with a second polar fluid to obtain a white precipitant and a spent polar liquid.

18. A process according to claim 17 wherein said polar fluid is acetone or a water/acetone mixture.

19. A process for making bis(haloarylsulfonyl) aromatics comprising contacting a stoichiometric excess of haloarylsulfonyl halide with an aromatic-bearing hydrocarbon selected from the group consisting of unsubstituted aromatics and alkyl substituted aromatics at a process temperature in the range of 100° to 200° C. and the presence of an aluminum chloride catalyst, wherein the aluminum chloride catalyst to aromatic-bearing hydrocarbon molar ratio is about 0.01:1 to about 0.10:1, thereby producing a precipitant and a spent liquor as products, (b) cooling said products by quenching and refluxing with a first polar fluid, (c) separating said precipitant, and (d) washing said precipitant one or more times with a second polar fluid to obtain a white precipitant and a spent polar liquid.

20. A process according to claim 19 wherein said process temperature is in the range of about 150° to about 200° C.

21. A process according to claim 20 wherein the haloarylsulfonyl halide to aromatic-bearing hydrocarbon molar ratio is about 2.3:1, said catalyst to aromatic-bearing hydrocarbon molar ratio is about 0.06:1, said temperature is about 180° C., and said haloarylsulfonyl halide is a haloarylsulfonyl chloride.

22. A process according to claim 21 wherein said aromatic-bearing hydrocarbon is an unsubstituted aromatic compound and said haloarylsulfonyl chloride is a 4-halobenzene sulfonyl chloride.

23. A process according to claim 22 wherein said aromatic-bearing hydrocarbon is biphenyl.

24. A process according to claim 19 wherein the haloarylsulfonyl halide to aromatic-bearing hydrocarbon ratio is about 2.4:1 to about 2.8:1.

25. A process according to claim 24 wherein said haloarylsulfonyl halide to aromatic-bearing hydrocarbon ratio is about 2.7:1 and said haloarylsulfonyl halide is a haloarylsulfonyl chloride.

26. A process according to claim 25 wherein said aromatic-bearing hydrocarbon is an unsubstituted aromatic compound and said haloarylsulfonyl chloride is a 4-halobenzene sulfonyl chloride.

27. A process according to claim 26 wherein said aromatic-bearing hydrocarbon is biphenyl.

28. A process according to claim 27 wherein said haloarylsulfonyl chloride is 4-chlorobenzene sulfonyl chloride.

29. A process for making 4,4'-bis(4-chlorophenylsulfonyl)biphenyl comprising contacting 4-chlorobenzene sulfonyl chloride with biphenyl at a stoichiometric molar ratio of about 2.3:1 in the presence of aluminum chloride catalyst at a catalyst to biphenyl molar ratio of about 0.06:1 and a process temperature of about 180° C. thereby producing a precipitant and a spent liquor as products, (b) cooling said products by quenching and refluxing with a first polar fluid, (c) separating said precipitant, and (d) washing said precipitant one or more times with a second polar fluid to obtain a white precipitant and a spent polar liquid.

30. A process for making 4,4'-bis(4-chlorophenylsulfonyl)biphenyl comprising contacting 4-chlorobenzene sulfonyl chloride with biphenyl at a stoichiometric molar ratio of about 2.7:1 in the presence of an aluminum chloride catalyst at a catalyst to biphenyl molar ratio of about 0.06:1 and a process temperature of about 180° C. thereby producing a precipitant and a spent liquor as products, (b) cooling said products by quenching and refluxing with a first polar fluid, (c) separating said precipitant, and (d) washing said precipitant one or more times with a second polar fluid to obtain a white precipitant.

31. A process for making polymer-grade bis(haloarylsulfonyl) aromatic compounds comprising the steps of:
   (a) contacting a stoichiometric excess of haloarylsulfonyl halide with an aromatic-bearing hydrocarbon selected from the group consisting of unsubstituted aromatic compounds and alkyl-substituted aromatic compounds in the presence of nitrobenzene solvent at a solvent to aromatic-bearing hydrocarbon molar ratio of 0.05:1 to 10:1, a process temperature in the range of 100° to 200° C., and in the presence of a ferric chloride catalyst at a ferric chloride catalyst to aromatic-bearing hydrocarbon molar ratio of about 0.0001 to about 0.05:1 thereby producing a precipitant and a spent liquor,
   (b) separating said precipitant,
   (c) washing said precipitant one or more times with a polar liquid to obtain a washed precipitant and a spent polar liquid, and
   (d) pressure recrystallizing said washed precipitant by contacting with methylene chloride to obtain a polymer-grade product.

32. A process according to claim 31 wherein said pressure recrystallizing comprises dissolving said washed precipitant in said methylene chloride at a temperature of about 140° C. and a pressure of about 210 psig and then recrystallizing by cooling to a temperature in the range of about 40° to 50° C. to obtain a polymer-grade product.

33. A process according to claim 31 additionally comprising the step of cooling said precipitant and spent liquor of step (a) by quenching and refluxing with a polar fluid.

34. A process according to claim 32 additionally comprising the step of cooling said precipitant and spent liquor of step (a) by quenching and refluxing with a polar fluid.

35. A process for making polymer-grade 4,4'-bis(4-chlorophenylsulfonyl)biphenyl comprising the steps of:
   (a) contacting 4-chlorobenzene sulfonyl chloride with biphenyl at a stoichiometric molar ratio of about 2.3:1, said contacting being in the presence of nitrobenzene at a nitrobenzene to biphenyl molar ratio of about 4.0:1, in the presence of ferric chloride catalyst at a catalyst to biphenyl molar ratio of about 0.005:1, and at a process temperature of about 140° C. thereby producing a precipitant and a spent liquor,
   (b) separating said precipitant from said spent liquor,
   (c) washing said precipitant one or more times with a polar liquid to obtain a washed precipitant, and
   (d) pressure recrystallizing said washed precipitant by contacting with methylene chloride to obtain a polymer-grade product.

36. A process according to claim 35 wherein said pressure recrystallizing comprises dissolving said washed precipitant in said methylene chloride at a temperature of about 140° C. and a pressure of about 210 psig and then recrystallizing by cooling to a temperature in the range of about 40° to 50° C. to obtain a polymer-grade product.

37. A process according to claim 36 additionally comprising the step of cooling said precipitant and spent liquor of step (a) by quenching and refluxing with a polar fluid.

38. A process for making polymer-grade bis(haloarylsulfonyl) aromatic compounds comprising the steps of:
   (a) contacting haloarylsulfonyl halide in the absence of an extraneous solvent with aromatic-bearing hydrocarbon selected from the group consisting of unsubstituted aromatic compounds and alkyl-substituted aromatic compounds wherein the haloarylsulfonyl halide to aromatic-bearing hydrocarbon molar ratio is at least 2.4:1, the process temperature is in the range of 100° to 200° C., and in the presence of a ferric chloride catalyst at a catalyst to aromatic-bearing hydrocarbon molar ratio of about 0.001 to about 0.01:1 thereby producing a precipitant and a spent liquor,
   (b) separating said precipitant,
   (c) washing said precipitant one or more times with a polar liquid to obtain a washed precipitant and a spent polar liquid, and
   (d) pressure recrystallizing said washed precipitant by contacting with methylene chloride to obtain a polymer-grade product.

39. A process according to claim 38 wherein said pressure recrystallizing comprises dissolving said washed precipitant in said methylene chloride at a temperature of about 140° C. and a pressure of about 210 psig and then recrystallizing by cooling to a temperature in the range of about 40° to 50° C. to obtain a polymer-grade product.

40. A process according to claim 38 additionally comprising the step of cooling said precipitant and spent liquor of step (a) by quenching and refluxing with a polar fluid.

41. A process for making polymer-grade 4,4'-bis(4-chlorophenylsulfonyl)biphenyl comprising the steps of:
   (a) contacting 4-chlorobenzene sulfonyl chloride with biphenyl at a stoichiometric molar ratio of about 2.66:1 in the presence of a ferric chloride catalyst at a catalyst to biphenyl molar ratio of about 0.005:1 and a process temperature of about 150° C. thereby producing a precipitant and a spent liquor,
   (b) separating said precipitant,
   (c) washing said precipitant one or more times with a polar liquid to obtain a washed precipitant and a spent polar liquid, and
   (d) pressure recrystallizing said washed precipitant by contacting with methylene chloride to obtain a polymer-grade product.

42. A process according to claim 41 wherein said pressure recrystallizing comprises dissolving said washed precipitant in said methylene chloride at a temperature of about 140° C. and a pressure of about 210 psig and then recrystallizing by cooling to a temperature in the range of about 40° to 50° C. to obtain a polymer-grade product.

43. A process according to claim 42 additionally comprising the step of cooling said precipitant and spent liquor of step (a) by quenching and refluxing with a polar fluid.

44. A process for making polymer-grade bis(haloarylsulfonyl) aromatics comprising the steps of:
   (a) contacting a stoichiometric excess of haloarylsulfonyl halide with an aromatic-bearing hydrocarbon selected from the group consisting of unsubstituted aromatic compounds and alkyl substituted aromatic compounds at a process temperature in the range of 100° to 200° C. and in the presence of an aluminum chloride catalyst at a concentration effective to catalyze the reaction thereby producing a precipitant and a spent liquor, (b) separating said precipitant, (c) washing said precipitant one or more times with a polar liquid to obtain a washed precipitant and a spent polar liquid, and (d) pressure recrystallizing said washed precipitant by contacting with methylene chloride to obtain a polymer-grade product.

45. A process according to claim 44 wherein said pressure recrystallizing comprises dissolving said washed precipitant in said methylene chloride at a temperature of about 140° C. and a pressure of about 210 psig and then recrystallizing by cooling to a temperature in the range of about 40° to 50° C. to obtain a polymer-grade product.

46. A process according to claim 44 additionally comprising the step of cooling said precipitant and spent liquor of step (a) by quenching and refluxing with a polar fluid.

47. A process for making polymer-grade 4,4'-bis(4-chlorophenylsulfonyl)biphenyl comprising the steps of:

(a) contacting 4-chlorobenzene sulfonyl chloride with biphenyl at a stoichiometric molar ratio of about 2.3:1 in the presence of aluminum chloride catalyst at a catalyst to biphenyl molar ratio of about 0.06:1 and a process temperature of about 180° C. thereby producing a precipitant and a spent liquor, (b) separating said precipitant, (c) washing said precipitant one or more times with a polar liquid to obtain a washed precipitant and a spent polar liquid, and (d) pressure recrystallizing said washed precipitant by contacting with methylene chloride to obtain a polymer-grade product.

48. A process according to claim 47 wherein said pressure recrystallizing comprises dissolving said washed precipitant in said methylene chloride at a temperature of about 140° C. and a pressure of about 210 psig and then recrystallizing by cooling to a temperature in the range of about 40° to 50° C. to obtain a polymer-grade product.

49. A process according to claim 48 additionally comprising the step of cooling said precipitant and spent liquor of step (a) by quenching and refluxing with a polar fluid.

50. A process for making polymer-grade 4,4'-bis(4-chlorophenylsulfonyl)biphenyl comprising the steps of:

(a) contacting 4-chlorobenzene sulfonyl chloride with biphenyl at a stoichiometric molar ratio of about 2.7:1 in the presence of an aluminum chloride catalyst at a catalyst to biphenyl molar ratio of about 0.06:1 and a process temperature of about 180° C. thereby producing a precipitant and a spent liquor, (b) separating said precipitant, (c) washing said precipitant one or more times with a polar liquid to obtain a washed precipitant and a spent polar liquid, and (d) pressure recrystallizing said washed precipitant by contacting with methylene chloride to obtain a polymer-grade product.

51. A process according to claim 50 wherein said pressure recrystallizing comprises dissolving said washed precipitant in said methylene chloride at a temperature of about 140° C. and a pressure of about 210 psig and then recrystallizing by cooling to a temperature in the range of about 40° to 50° C. to obtain a polymer-grade product.

52. A process according to claim 51 additionally comprising the step of cooling said precipitant and spent liquor of step (a) by quenching and refluxing with a polar fluid.

* * * * *